United States Patent
Kobayashi et al.

(10) Patent No.: US 11,628,134 B2
(45) Date of Patent: Apr. 18, 2023

(54) CELLULOSE ACETATE PARTICLES, COSMETIC COMPOSITION, AND METHOD OF PRODUCING CELLULOSE ACETATE PARTICLES

(71) Applicant: DAICEL CORPORATION, Osaka (JP)

(72) Inventors: Keiko Kobayashi, Tokyo (JP); Masaya Omura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 16/616,160

(22) PCT Filed: Feb. 6, 2019

(86) PCT No.: PCT/JP2019/004230
§ 371 (c)(1),
(2) Date: Nov. 22, 2019

(87) PCT Pub. No.: WO2019/156116
PCT Pub. Date: Aug. 15, 2019

(65) Prior Publication Data
US 2020/0179261 A1    Jun. 11, 2020

(30) Foreign Application Priority Data

Feb. 7, 2018 (JP) .............................. JP2018-020422
May 23, 2018 (JP) .............................. JP2018-099033

(51) Int. Cl.
*A61K 8/73* (2006.01)
*A61Q 1/10* (2006.01)
(Continued)

(52) U.S. Cl.
CPC ................ *A61K 8/731* (2013.01); *A61K 8/36* (2013.01); *A61K 8/732* (2013.01); *A61K 8/817* (2013.01);
(Continued)

(58) Field of Classification Search
None
See application file for complete search history.

(56) References Cited

U.S. PATENT DOCUMENTS 5,047,180 A    9/1991  Steiner et al.
5,064,949 A *  11/1991 Steiner ..................... C08B 3/22
                                                  536/56

(Continued)

FOREIGN PATENT DOCUMENTS

CN     102911379 A     2/2013
EP     0 750 007 A1   12/1996
(Continued)

OTHER PUBLICATIONS

Tanwar. Brazilian Journal of Pharmaceutical Sciences.vol. 43, n. 4, out./dez., 2007. p. 549-534.*

(Continued)

*Primary Examiner* — Nicole P Babson
*Assistant Examiner* — Lori K Mattison
(74) *Attorney, Agent, or Firm* — Birch, Stewart, Kolasch & Birch, LLP (57) ABSTRACT

An object of the present invention is to provide fine particles excellent in biodegradability and touch feeling. Disclosed are cellulose acetate particles, the cellulose acetate particles have an average particle size of 80 nm or more and 100 μm or less, a sphericity of 0.7 or more and 1.0 or less, and a surface smoothness of 80% or more and 100% or less, and the cellulose acetate has a total degree of acetyl substitution of 0.7 or more and 2.9 or less.

25 Claims, 2 Drawing Sheets

(51) Int. Cl.
*A61Q 17/04* (2006.01)
*C08B 3/06* (2006.01)
*A61K 8/36* (2006.01)
*A61K 8/81* (2006.01)
*A61Q 1/12* (2006.01)
*A61Q 1/02* (2006.01)
*A61K 8/02* (2006.01)
*C08J 3/12* (2006.01)

(52) U.S. Cl.
CPC .............. *A61Q 1/10* (2013.01); *A61Q 1/12* (2013.01); *A61Q 17/04* (2013.01); *A61K 8/0241* (2013.01); *A61K 2800/412* (2013.01); *A61Q 1/02* (2013.01); *C08J 3/12* (2013.01)

(56) References Cited

U.S. PATENT DOCUMENTS

| | | | |
|---|---|---|---|
| 5,686,113 A * | 11/1997 | Speaker | A61K 9/1652 424/490 |
| 2005/0239925 A1 | 10/2005 | Ito | |
| 2009/0098288 A1 | 4/2009 | Massa et al. | |
| 2009/0170981 A1 | 7/2009 | Ito | |
| 2010/0247914 A1* | 9/2010 | Enomoto | A61K 8/25 428/402 |
| 2014/0013999 A1* | 1/2014 | Goerlach-Doht | C08J 3/05 536/91 |
| 2014/0113826 A1* | 4/2014 | Fallon | A61Q 19/00 504/358 |
| 2016/0355662 A1 | 12/2016 | Tokuoka et al. | |
| 2018/0037670 A1 | 2/2018 | Higuchi et al. | |

FOREIGN PATENT DOCUMENTS

| | | | | |
|---|---|---|---|---|
| JP | 59-181205 A | 10/1984 | | |
| JP | 59-219333 A | 12/1984 | | |
| JP | 61-211342 A | 9/1986 | | |
| JP | 2001-137100 A | 5/2001 | | |
| JP | 2004-51942 A | 2/2004 | | |
| JP | 2004-269865 A | 9/2004 | | |
| JP | 2007-224259 A | 9/2007 | | |
| JP | 2016-500129 A | 1/2016 | | |
| JP | 6187653 B1 | 8/2017 | | |
| KR | 10-1555861 B1 | 9/2015 | | |
| WO | WO-0235991 A2 * | 5/2002 | ........... | A61K 9/1694 |
| WO | WO 2014/066463 A1 | 5/2014 | | |
| WO | WO 2016/135778 A1 | 9/2016 | | |

OTHER PUBLICATIONS

Zhao. Industrial Biotechnology. vol. 11 No. 1 . Feb. 2015. p. 34-44.*
Decision to Grant a Patent for Japanese Application No. 2019-538544, dated Oct. 1, 2019.
International Search Report, issued in PCT/JP2019/004230, PCT/ISA/210, dated Apr. 9, 2019.
Written Opinion of the International Searching Authority, issued in PCT/JP2019/004230, PCT/ISA/237, dated Apr. 9, 2019.
Annex of Documents D1 through D16, MB04, 2022, 14 pages total.
European Communication of a notice of opposition for European Application No. 19751764.2, dated Oct. 31, 2022, with an English translation.
OBrien et al., "Continuous Production of Cellulose Microbeads via Membrane Emulsification," ACS Sustainable Chemistry & Engineering, vol. 5, 2017, pp. 5931-5939.
Thümmler, "Production, Characterization and Modification of Pearl Cellulose," [Dissertation], TU Dresden, Feb. 22, 2012, 330 pages total, with an English translation.
Lubkoll, "We use two different regulations according to EP 0 750 007 A1," [Affidavit], 1996, 7 pages total.
Petsitis, "Microplastic in Cosmetics—Alternatives for the sensory Profile," Euro Cosmetics, 2009, 13 pages total, with an English translation.

* cited by examiner

CELLULOSE ACETATE PARTICLES, COSMETIC COMPOSITION, AND METHOD OF PRODUCING CELLULOSE ACETATE PARTICLES

TECHNICAL FIELD

The present invention relates to cellulose acetate particles, cosmetic compositions, and a method of producing cellulose acetate particles.

BACKGROUND ART

Conventionally, various polymer microparticles according to the intended use have been proposed. For example, the fine particles are contained in cosmetics for various purposes. The purpose of containing fine particles in cosmetics is to improve spread of the cosmetics, to change the touch feeling, to impart wrinkle blurring effects, to improve slippage of foundation and the like, and the like.

Particularly, fine particles having high sphericity are excellent in touch feeling, and a light scattering (soft focus) effect can be obtained depending on the physical properties and shape thereof. When such fine particles are used for foundation and the like, it is possible to expect the effect (soft focus effect) of filling irregularities of the skin with the fine particles to smooth the irregularities, and scattering light in various directions to make wrinkles and the like inconspicuous.

For such purposes and effects of cosmetics, fine particles to be blended in cosmetics are required to be fine particles having narrow particle size distribution and high sphericity, and as such fine particles, fine particles made of synthetic polymers such as polyamide such as Nylon 12; polymethyl methacrylate (PMMA); and polystyrene (PS) have been proposed.

However, fine particles made of those synthetic polymers have a low relative density such as 1 or less and are too small in particle size. Consequently, the fine particles tend to float in water and may not be able to be removed in sewage-treatment plant, so that the fine particles may flow directly into a river or into the sea through a river. Thus, there is a problem that the ocean, etc. are polluted with the fine particles made of those synthetic polymers.

In addition, since the fine particles made of those synthetic polymers have the property of adsorbing a trace amount of chemical pollutants in the environment, there are concerns that various effects may occur, for example, the plankton and fish having taken the fine particles with the chemical pollutants may adversely affect the human body.

From such a concern, attempts have been made to replace fine synthetic polymer particles used in various applications with biodegradable particles.

Cellulose acetate is a typical biodegradable polymer. Cellulose acetate is excellent in that it can be obtained from natural materials, such as wood and cotton, which do not conflict with food and feed. Thus, it would be beneficial if fine synthetic polymer particles could be replaced with cellulose acetate fine particles. However, polymers to which a method of producing fine synthetic polymer particles is applicable are limited, and it is difficult to apply the method to production of fine cellulose acetate particles.

PTL 1 discloses a method including forming a polysaccharide ester product from a polysaccharide synthesis, in which the polysaccharide ester product contains a polysaccharide ester and a solvent; diluting the polysaccharide ester product, thereby yielding a polysaccharide ester dope; and forming a plurality of polysaccharide ester microspheres from the polysaccharide ester dope, and examples of articles which may contain polysaccharide ester microspheres include cosmetic compositions.

PTL 2 describes cellulose acylate whose volume average particle size D50 measured using a laser diffraction type particle size distribution measuring device is 72 μm or more and 100 μm or less, polymerization degree is 131 or more and 350 or less, and substitution degree is 2.1 or more and 2.6 or less. PTL 2 further describes that a method of producing the cellulose acylate preferably includes an acylation step of acylating cellulose in the presence of sulfuric acid, and a deacylation step of deacylating the acylated cellulose in the presence of acetic acid in a polar solvent.

PTL 3 describes that a molded article (e.g., a porous material, and a spherical particle) containing (A) a resin component is produced by kneading the resin component (A) such as a thermoplastic resin and a water-soluble auxiliary component (B) to prepare a dispersed composition, and eluting the auxiliary component (B) from the dispersed composition. PTL 3 further describes a cellulose derivative such as cellulose acetate as the resin component (A).

CITATION LIST

Patent Literature

PTL 1: JP 2016-500129 T
PTL 2: Japanese Patent No. 6187653
PTL 3: JP 2004-051942 A

SUMMARY OF INVENTION

Technical Problem

However, the polysaccharide ester microspheres of PTL 1 are porous particles having a large particle size and a broad particle size distribution, and are not sufficient as a substitute for fine synthetic polymer particles to be blended in cosmetics and the like. Moreover, the cellulose acylate obtained by the producing method described in PTL 2 is amorphous and porous particles. Furthermore, a particulate molded article obtained by the producing method described in PTL 3 corresponds to particles having low sphericity and a substantially spherical shape.

An object of the present invention is to provide fine particles excellent in biodegradability and touch feeling.

Solution to Problem

A first aspect of the present invention relates to cellulose acetate particles having an average particle size of 80 nm or more and 100 μm or less, a sphericity of 0.7 or more and 1.0 or less, and a surface smoothness of 80% or more and 100% or less, and the cellulose acetate has a total degree of acetyl substitution of 0.7 or more and 2.9 or less.

In the cellulose acetate particles, the total degree of acetyl substitution of the cellulose acetate may be 2.0 or more and less than 2.6.

The cellulose acetate particles may contain a plasticizer, and a content of the plasticizer may be 2% by weight or more and 40% by weight or less based on a weight of the cellulose acetate particles.

In the cellulose acetate particles, the plasticizer may be at least one or more selected from the group consisting of a citric acid-based plasticizer, a glycerin ester-based plasticizer, an adipic acid-based plasticizer, and a phthalic acid-based plasticizer.

A second aspect of the present invention relates to a cosmetic composition containing the cellulose acetate particles.

A third aspect of the present invention relates to a method of producing cellulose acetate particles, the method including mixing cellulose acetate having a total degree of acetyl substitution of 0.7 or more and 2.9 or less with a plasticizer to obtain cellulose acetate impregnated with the plasticizer, kneading cellulose acetate impregnated with the plasticizer and a water-soluble polymer at 200° C. or more and 280° C. or less to obtain a dispersion having the cellulose acetate impregnated with the plasticizer as a dispersoid, and removing the water-soluble polymer from the dispersion.

In the method of producing cellulose acetate particles, the mixing may be performed by mixing the cellulose acetate and the plasticizer in a temperature range of 20° C. or more and less than 200° C. and then melt-kneading.

In the method of producing cellulose acetate particles, the plasticizer may be at least one or more selected from the group consisting of a citric acid-based plasticizer, a glycerin ester-based plasticizer, an adipic acid-based plasticizer, and a phthalic acid-based plasticizer.

In the method of producing cellulose acetate particles, the plasticizer may be at least one or more selected from the group consisting of triethyl citrate, acetyl triethyl citrate, acetyl tributyl citrate, triacetin, and diisononyl adipate.

In the method of producing cellulose acetate particles, the plasticizer may be at least one or more selected from the group consisting of acetyl triethyl citrate, triacetin, diacetin, and diethyl phthalate.

In the method of producing cellulose acetate particles, the water-soluble polymer may be polyvinyl alcohol or thermoplastic starch.

Advantageous Effects of Invention

The present invention can provide fine particles excellent in biodegradability and touch feeling.

DESCRIPTION OF EMBODIMENTS

Cellulose Acetate Particles

Cellulose acetate particles of the present disclosure have an average particle size of 80 nm or more and 100 μm or less, a sphericity of 0.7 or more and 1.0 or less, and a surface smoothness of 80% or more and 100% or less, and the cellulose acetate has a total degree of acetyl substitution of 0.7 or more and 2.9 or less.

While the cellulose acetate particles of the present disclosure have an average particle size of 80 nm or more and 100 μm or less, the average particle size may be 100 nm or more, 1 μm or more, 2 μm or more, or 4 μm or more. On the other hand, the average particle size may be 80 μm or less, 40 μm or less, 20 μm or less, or 14 μm or less. When the average particle size is too large, a light scattering (soft focus) effect becomes lower as well as touch feeling is poor. On the other hand, when the average particle size is too small, the production becomes difficult. Examples of the touch feeling include touch feeling on directly touching cellulose acetate particles and sensorial feeling and touch feeling obtained when the cellulose acetate particles are blended in a cosmetic composition The average particle size can be measured using dynamic light scattering. The specific procedure is as follows. First, a sample is prepared by converting 100 ppm concentration of cellulose acetate particles into a pure water suspension using an ultrasonic vibrator. After that, the average particle size can be measured by measuring volume frequency particle size distribution using a laser diffraction method (Horiba, Ltd. "Laser Diffraction/Scattering Particle Size Distribution Measurement Device LA-960", ultrasonication for 15 minutes, refractive index (1.500, medium (water; 1.333)). The average particle size (nm, μm, etc.) herein refers to a value of the particle size corresponding to a cumulative 50% scattering intensity in the particle size distribution.

A particle size variation coefficient of the cellulose acetate particles of the present disclosure may be 0% or more and 60% or less or 2% or more and 50% or less.

The particle size variation coefficient (%) can be calculated by standard deviation of particle size/average particle size×100.

While the sphericity of the cellulose acetate particles of the present disclosure is 0.7 or more and 1.0 or less, the sphericity is preferably 0.8 or more and 1.0 or less and more preferably 0.9 or more and 1.0 or less. When the sphericity is less than 0.7, the touch feeling is poor, and for example, when the cellulose acetate particles are blended in a cosmetic composition, sensorial feeling and the soft focus effect are reduced.

The sphericity can be measured by the following method. Major axis and minor axis of 30 randomly selected particles are measured using an image of particles observed with a scanning electron microscope (SEM), a minor axis/major axis ratio of each particle is determined, and an average value of the minor axis/major axis ratios is taken as the sphericity. It can be determined that as the sphericity gets closer to 1, the particle becomes more true spherical.

While the surface smoothness of the cellulose acetate particles of the present disclosure is 80% or more and 100% or less, the surface smoothness is preferably 85% or more and 100% or less and more preferably 90% or more and 100% or less. If the surface smoothness is less than 80%, the touch feeling is poor. The closer to 100%, the better the touch feeling.

The surface smoothness can be determined based on an area of a recess by taking a scanning electron micrograph of the particle and observing unevenness of the particle surface.

While the cellulose acetate of the cellulose acetate particles of the present disclosure has a total degree of acetyl substitution of 0.7 or more and 2.9 or less, the total degree of acetyl substitution is preferably 0.7 or more and less than 2.6, more preferably 1.0 or more and less than 2.6, still more preferably 1.4 or more and less than 2.6, and most preferably 2.0 or more and less than 2.6.

When the total degree of acetyl substitution is less than 0.7, the water solubility is high, and in a step of extracting particles in the production of the cellulose acetate particles to be described later and, in particular in a step of removing a water-soluble polymer from a dispersion, cellulose acetate tends to be eluted, so that particle sphericity may decrease which may result in poor touch feeling. On the other hand, when the total degree of acetyl substitution is more than 2.9, biodegradability of the cellulose acetate particles is poor.

The total degree of acetyl substitution of cellulose acetate can be measured by the following method. First, the total degree of acetyl substitution is the total of the degrees of acetyl substitution at the 2-, 3-, and 6-positions of the glucose ring of the cellulose acetate, and the degrees of acetyl substitution at the 2-, 3-, and 6-positions of a glucose ring of cellulose acetate particles can be measured by NMR technique according to the Tezuka's method in Carbohydr. Res. 273, 83(1995). Specifically, free hydroxy groups of a cellulose acetate sample are propionylated with propionic anhydride in pyridine. The resulting sample is dissolved in deuterated chloroform and subjected to $^{13}$C-NMR spectral measurement. Carbon signals of acetyl group appear in the order of the 2-position, 3-position, and 6-position from a higher magnetic field in a region of from 169 ppm to 171 ppm, and carbonyl carbon signals of propionyl group appear in the same order in a region of from 172 ppm to 174 ppm. The degrees of acetyl substitution at the 2-, 3-, and 6-positions in the glucose ring of the original cellulose acetate can be determined on the basis of relative abundances between acetyl group and propionyl group at the corresponding positions. The degree of acetyl substitution can be analyzed not only by $^{13}$C-NMR, but also by $^{1}$H-NMR.

In addition, the total degree of acetyl substitution may be determined by determining an acetylation degree according to a method of measuring an acetylation degree prescribed in ASTM D-817-91 (Standard Test Methods of Testing Cellulose Acetates) and converting the acetylation degree into the total degree of acetyl substitution according to a formula below. This is a most common method for determining the degree of substitution of cellulose acetate.

$$DS=162.14 \times AV \times 0.01/(60.052-42.037 \times AV \times 0.01)$$

In the above formula, DS represents the total degree of acetyl substitution, and AV represents the acetylation degree (%). A value of the degree of substitution obtained by conversion may usually be somewhat different from the value measured by NMR described above. If the conversion value and the value measured by NMR are different from each other, the value measured by NMR is adopted. If the values measured by various NMR methods are different from each other, the value measured according to the method of Tezuka is prior to the other values.

An outline of the method of measuring the acetylation degree prescribed in ASTM D-817-91 (Standard Test Methods of Testing Cellulose Acetates) is as follows. Dry cellulose acetate in an amount of 1.9 g is precisely weighed and dissolved in 150 ml of a mixed solvent of acetone and dimethyl sulfoxide (volume ratio 4:1). Then, 30 ml of a 1N-sodium hydroxide aqueous solution is added thereto, and the resulting mixture is saponified at 25° C. for two hours. Phenolphthalein is added as an indicator, and the excess sodium hydroxide is titrated with 1N-sulfuric acid (concentration factor: F). Also, a blank test is performed in the same manner as above, and the acetylation degree is calculated according to a formula below.

$$\text{Average acetylation degree (\%)} = \{6.5 \times (B-A) \times F\}/W$$

(In the formula, A represents the titer (ml) of 1N-sulfuric acid used for the sample; B represents the titer (ml) of 1N-sulfuric acid in the blank test; F represents the concentration factor of 1N-sulfuric acid; and W represents the weight of the sample.)

The cellulose acetate particles of the present disclosure may have a bulk density of 0.1 or more and 0.9 or less or 0.5 or more and 0.9 or less. For example, when the particles are blended in cosmetics, the higher the bulk density of the particles, the better the fluidity of the cosmetic composition. The bulk density can be measured by the method according to JIS K 1201-1.

The cellulose acetate particles of the present disclosure may or may not contain a plasticizer. In the present disclosure, a plasticizer refers to a compound capable of increasing plasticity of cellulose acetate. The plasticizer is not particularly limited and examples thereof include adipic acid-based plasticizers containing adipic acid ester such as dimethyl adipate, dibutyl adipate, diisostearyl adipate, diisodecyl adipate, diisononyl adipate, diisobutyl adipate, diisopropyl adipate, diethylhexyl adipate, dioctyl adipate, dioctyldodecyl adipate, dicapryl adipate, and dihexyldecyl adipate; citric acid-based plasticizers containing citric acid ester such as acetyl triethyl citrate, acetyl tributyl citrate, isodecyl citrate, isopropyl citrate, triethyl citrate, triethylhexyl citrate, and tributyl citrate; glutaric acid-based plasticizers containing glutaric acid ester such as diisobutyl glutarate, dioctyl glutarate, and dimethyl glutarate; succinic acid-based plasticizers containing succinic acid ester such as diisobutyl succinate, diethyl succinate, diethylhexyl succinate, and dioctyl succinate; sebacic acid-based plasticizers containing sebacic acid ester such as diisoamyl sebacate, diisooctyl sebacate, diisopropyl sebacate, diethyl sebacate, diethylhexyl sebacate, and dioctyl sebacate; glycerin ester-based plasticizers containing glycerin alkyl ester such as triacetin, diacetin, and monoacetin; neopentyl glycol; phthalic acid-based plasticizers containing phthalate ester such as ethyl phthalate, methyl phthalate, diaryl phthalate, diethyl phthalate, diethylhexyl phthalate, dioctyl phthalate, dibutyl phthalate, and dimethyl phthalate; and phosphoric acid-based plasticizers containing phosphoric acid ester such as trioleyl phosphate, tristearyl phosphate, and tricetyl phosphate. In addition, examples thereof include di-2-methoxyethyl phthalate tartaric acid dibutyl 0-benzoyl ethyl benzoate, ethyl phthalyl ethyl glycolate (EPEG), methyl phthalyl ethyl glycolate (MPEG), N-ethyl toluene sulfonamide, p-toluenesulfonic acid 0-cresyl phosphate triethyl (TEP), triphenyl phosphate (TPP), and tripropionin. These plasticizers may be used alone or in a combination of two or more kinds thereof.

Among these, preferred are at least one or more selected from the group consisting of citric acid-based plasticizers containing citric acid ester such as triethyl citrate, acetyl triethyl citrate, and acetyl tributyl citrate; glycerin ester-based plasticizers containing glycerin alkyl ester such as triacetin, diacetin, and monoacetin; adipic acid-based plasticizers such as diisononyl adipate; and phthalic acid-based plasticizers such as ethyl phthalate and methyl phthalate. More preferred are at least one or more selected from the group consisting of triethyl citrate, acetyl triethyl citrate, acetyl tributyl citrate, triacetin, and diisononyl adipate. Still more preferred are at least one or more selected from the group consisting of acetyl triethyl citrate, triacetin, diacetin and diethyl phthalate. However, phthalic acid-based plasticizers need to be used with caution because they may be similar to environmental hormones.

When the cellulose acetate particles contain a plasticizer, the content of the plasticizer contained in the cellulose acetate particles is not particularly limited. For example, the content of the plasticizer may be more than 0% by weight and 40% by weight or less, 2% by weight or more and 40% by weight or less, 10% by weight or more and 30% by weight or less, or 15% by weight or more and 20% by weight or less based on the weight of the cellulose acetate particles.

The content of the plasticizer in the cellulose acetate particles is determined by $^{1}$H-NMR measurement.

The cellulose acetate particles of the present disclosure are excellent in biodegradability. The biodegradation rate is preferably 40% by weight or more, more preferably 50% by weight or more, and still more preferably 60% by weight or more within 30 days.

The biodegradation rate can be measured by a method using activated sludge according to JIS K6950.

The cellulose acetate particles of the present disclosure can be produced by the production method described below.

The cellulose acetate particles of the present disclosure can be suitably used, for example, in cosmetic compositions because the cellulose acetate particles are excellent in biodegradability and touch feeling. In addition, since the cellulose acetate particles have a high sphericity, when the particles are blended in a cosmetic composition, it is possible to obtain the effect (soft focus effect) of filling irregularities of the skin with the particles to smooth the irregularities, and scattering light in various directions to make wrinkles and the like inconspicuous.

Examples of cosmetic compositions include foundation such as liquid foundation and powder foundation; concealers; sunscreens; makeup bases; lipsticks and lip primers; powders such as body powders, solid face powders, and face powders; solid powder eye shadows; wrinkle concealing creams; and skin and hair external preparations used mainly for cosmetic purposes such as skin care lotions, and the dosage form thereof is not particularly limited. The dosage form may be any of liquid agents such as aqueous solutions, emulsions, and suspensions; semi-solid agents such as gels and creams; and solid agents such as powders, granules and solids. In addition, the dosage form may be an emulsion dosage such as cream or a milky lotion; an oil gel dosage such as lipstick; a powder dosage such as foundation; or an aerosol dosage such as a hair styling agent.

Method of Producing Cellulose Acetate Particles

A method of producing cellulose acetate particles of the present disclosure includes mixing cellulose acetate having a total degree of acetyl substitution of 0.7 or more and 2.9 or less with a plasticizer to obtain cellulose acetate impregnated with the plasticizer, kneading cellulose acetate impregnated with the plasticizer and a water-soluble polymer at 200° C. or more and 280° C. or less to obtain a dispersion having the cellulose acetate impregnated with the plasticizer as a dispersoid, and removing the water-soluble polymer from the dispersion.

Step of Obtaining Cellulose Acetate Impregnated With Plasticizer

In the step of obtaining cellulose acetate impregnated with a plasticizer, cellulose acetate having a total degree of acetyl substitution of 0.7 or more and 2.9 or less is mixed with a plasticizer.

The cellulose acetate having a total degree of acetyl substitution of 0.7 or more and 2.9 or less can be produced by a known method of producing cellulose acetate. Examples of such a production method include the so-called acetic acid method using an acetic anhydride as an acetylating agent, an acetic acid as a diluent and a sulfuric acid as a catalyst. A basic process of the acetic acid method includes a pretreating step (1) of disintegrating and crushing a pulp raw material relatively high in α-cellulose content by proportion (dissolved pulp), and then spraying and blending acetic acid onto/into the resultant, an acetylating step (2) of causing the pretreated pulp in the step (1) to react with a mixed acid composed of acetic anhydride, acetic acid and an acetylating catalyst (such as sulfuric acid), a ripening step (3) of hydrolyzing the resultant cellulose acetate to prepare a cellulose acetate having a desired acetylation degree, and a post-treating step (4) of precipitating/separating the cellulose acetate, the hydrolysis reaction of which has been ended, from the reaction solution, and then purifying, stabilizing, and drying the separated cellulose acetate.

While the cellulose acetate has a total degree of acetyl substitution of 0.7 or more and 2.9 or less, the total degree of acetyl substitution is preferably 0.7 or more and less than 2.6, more preferably 1.0 or more and less than 2.6, still more preferably 1.4 or more and less than 2.6, and most preferably 2.0 or more and less than 2.6. The total degree of acetyl substitution can be adjusted by adjusting conditions of the ripening step (conditions such as time and temperature).

The plasticizer may be used without particular limitation as long as it has a plasticizing effect in melt extrusion processing of cellulose acetate, and specifically, the plasticizers exemplified as the plasticizer contained in cellulose acetate particles may be used alone or in a combination of two or more kinds thereof.

Among the exemplified plasticizers, preferred are at least one or more selected from the group consisting of citric acid-based plasticizers containing citric acid ester such as triethyl citrate, acetyl triethyl citrate, and acetyl tributyl citrate; glycerin ester-based plasticizers containing glycerin alkyl ester such as triacetin, diacetin, and monoacetin; adipic acid-based plasticizers such as diisononyl adipate; and phthalic acid-based plasticizers such as ethyl phthalate and methyl phthalate. More preferred are at least one or more selected from the group consisting of triethyl citrate, acetyl triethyl citrate, acetyl tributyl citrate, triacetin, and diisononyl adipate. Still more preferred are at least one or more selected from the group consisting of acetyl triethyl citrate, triacetin, diacetin and diethyl phthalate. However, phthalic acid-based plasticizers need to be used with caution because they may be similar to environmental hormones.

The amount of the plasticizer to be added may be more than 0 parts by weight and 40 parts by weight or less, 2 parts by weight or more and 40 parts by weight or less, 10 parts by weight or more and 30 parts by weight or less, or 15 parts by weight or more and 20 parts by weight or less with respect to 100 parts by weight of the total of cellulose acetate and the plasticizer. When the amount of the plasticizer is too small, the sphericity of the resulting cellulose acetate particles tends to decrease, and when the amount of the plasticizer is too large, the shape of the particles cannot be maintained, so that the sphericity tends to decrease.

The cellulose acetate and the plasticizer can be mixed by a dry or wet method using a mixer such as a Henschel mixer. When a mixer such as a Henschel mixer is used, the temperature in the mixer may be a temperature at which the cellulose acetate does not melt, for example, in a range of 20° C. or more and less than 200° C.

The cellulose acetate and the plasticizer may be mixed by melt-kneading. The melt-kneading may be performed in combination with mixing using a mixer such as a Henschel mixer, and in that case, preferably, the melt-kneading is performed after mixing is performed in the temperature range of 20° C. or more and less than 200° C. using a mixer such as a Henschel mixer. As the plasticizer and the cellulose acetate become more uniform and conform in a short time, the sphericity of the cellulose acetate particles that can be finally prepared becomes high, and the touch feeling and sensation are improved.

The melt-kneading is preferably performed by heating and mixing with an extruder. The kneading temperature (cylinder temperature) of the extruder may range from 200° C. to 230° C. Even in this temperature range, a uniform kneaded product can be obtained by plasticization. When the temperature is too low, the sphericity of the particles to be obtained decreases, so that the touch feeling and sensation are reduced, and when the temperature is too high, degeneration and coloring due to the heat of the kneaded product may occur. In addition, the viscosity of a melt may be reduced, which may result in insufficient kneading of a resin in a twin-screw extruder.

The melting point of cellulose acetate is approximately 230° C. to 280° C., though depending on the degree of substitution, and is close to a decomposition temperature of cellulose acetate, so that although melt-kneading is usually difficult in this temperature range, this is because cellulose acetate (flakes) impregnated with a plasticizer can lower a plasticization temperature. The kneading temperature (cylinder temperature) may be, for example, 200° C. when a twin-screw extruder is used. The kneaded product may be extruded in a strand form and formed into a pellet form by hot cutting or the like. The die temperature in this case may be approximately 220° C.

Step of Obtaining Dispersion

In the step of obtaining a dispersion, the cellulose acetate impregnated with the plasticizer and the water-soluble polymer are kneaded at 200° C. or more and 280° C. or less.

The cellulose acetate impregnated with the plasticizer and the water-soluble polymer can be kneaded by an extruder such as a twin-screw extruder. The kneading temperature refers to the cylinder temperature.

The dispersion may be extruded in the form of a string from a die attached to a tip of an extruder such as a twin-screw extruder and then cut into pellets. At this time, the die temperature may be 220° C. or more and 300° C. or less.

The amount of the water-soluble polymer to be added may be 55 parts by weight or more and 99 parts by weight or less with respect to 100 parts by weight of the total of the cellulose acetate impregnated with the plasticizer and the water-soluble polymer. The amount of the water-soluble polymer to be added is preferably 60 parts by weight or more and 90 parts by weight or less and more preferably 65 parts by weight or more and 85 parts by weight or less.

The water-soluble polymer in the present specification refers to a polymer having an insoluble content of less than 50% by weight when 1 g of the polymer is dissolved in 100 g of water at 25° C. Examples of the water-soluble polymers include polyvinyl alcohol, polyethylene glycol, sodium polyacrylate, polyvinyl pyrrolidone, polypropylene oxide, polyglycerin, polyethylene oxide, vinyl acetate, modified starch, thermoplastic starch, methyl cellulose, ethyl cellulose, hydroxyethyl cellulose, and hydroxypropyl cellulose. Among these water-soluble polymers, polyvinyl alcohol, polyethylene glycol and thermoplastic starch are preferable, and polyvinyl alcohol and thermoplastic starch are particularly preferable. The thermoplastic starch can be obtained by a well-known method. For example, JP-B-6-6307, WO 92/04408, etc. can be referred to, and more specifically, for example, Tapioca starch mixed with about 20% of glycerin as a plasticizer and kneaded with a twin-screw extruder or the like can be used.

The resulting dispersion is a dispersion having a water-soluble polymer as a dispersion medium and the cellulose acetate impregnated with the plasticizer as a dispersoid. In other words, the water-soluble polymer may be a sea component, and the cellulose acetate impregnated with the plasticizer may be an island component. In the dispersion, the kneaded product constituting the island component contains cellulose acetate and a plasticizer, and is mainly spherical.

Step of Removing Water-Soluble Polymer

The step of removing the water-soluble polymer from the dispersion is described.

The method of removing the water-soluble polymer is not particularly limited as long as the water-soluble polymer can be dissolved and removed from the particles, but for example, there is a method of dissolving and removing the water-soluble polymer of the dispersion using water; an alcohol such as methanol, ethanol, or isopropanol; or a solvent such as a mixed solution thereof. Specifically, for example, there is a method of removing the water-soluble polymer from the dispersion by mixing the dispersion and the solvent, filtering the mixture, and taking out a filter product.

In the step of removing the water-soluble polymer from the dispersion, the plasticizer may or may not be removed from the dispersion along with the water-soluble polymer. Thus, the resulting cellulose acetate particles may or may not contain a plasticizer.

In a mixing ratio of the dispersion to the solvent, the dispersion is preferably mixed in an amount of 0.01% by weight or more and 20% by weight or less, more preferably 2% by weight or more and 15% by weight or less, and still more preferably 4% by weight or more and 13% by weight or less with respect to the total weight of the dispersion and the solvent. If the dispersion content is higher than 20% by weight, dissolution of the water-soluble polymer becomes insufficient, and the water-soluble polymer cannot be removed by washing, or it becomes difficult to separate the cellulose acetate particles not dissolved in the solvent and the water-soluble polymer dissolved in the solvent by operation such as filtration or centrifugation.

The mixing temperature of the dispersion and the solvent is preferably 0° C. or more and 200° C. or less, more preferably 20° C. or more and 110° C. or less, and still more preferably 40° C. or more and 80° C. or less. If the temperature is lower than 0° C., solubility of the water-soluble polymer becomes insufficient, and it becomes difficult to remove the water-soluble polymer by washing. If the temperature exceeds 200° C., deformation and aggregation of particles occur, and it becomes difficult to take out the particles while maintaining a desired shape of the particles.

The mixing time of the dispersion and the solvent is not particularly limited and may be appropriately adjusted, but may be, for example, 0.5 hours or more, 1 hour or more, 3 hours or more, or 5 hours or more, and may be 6 hours or less.

The mixing method is not limited as long as the water-soluble polymer can be dissolved, but for example, by using a stirring apparatus such as an ultrasonic homogenizer or a three-one motor, the water-soluble polymer can be efficiently removed from the dispersion even at room temperature.

For example, when a three-one motor is used as the stirring apparatus, the number of rotations at the time of mixing of the dispersion and the solvent may be, for example, 5 rpm or more and 3000 rpm or less. Thereby, the water-soluble polymer can be more efficiently removed from the dispersion. In addition, the plasticizer can be efficiently removed from the dispersion.

EXAMPLES

Hereinafter, the present invention is specifically described with reference to Examples, but the technical scope of the present invention is not limited by these Examples.

Example A-1

100 parts by weight of cellulose diacetate (from Daicel Corporation: total degree of acetyl substitution DS=2.4) and 25 parts by weight of triacetin as a plasticizer were dry blended, dried at 80° C. for 12 hours or more, and further stirred and mixed using a Henschel mixer to obtain a mixture of cellulose acetate and the plasticizer. The obtained mixture was supplied to a twin-screw extruder (PCM 30 from Ikegai Corp, cylinder temperature: 200° C., die temperature: 220° C.), melt-kneaded, and extruded and pelletized to obtain a kneaded product.

30 parts by weight of a pellet of the obtained kneaded product and 70 parts by weight of polyvinyl alcohol (from The Nippon Synthetic Chemical Industry Co., Ltd.: melting point 190° C., degree of saponification 99.1%) as a water-soluble polymer were dry blended and then supplied to a twin-screw extruder (PCM 30 from Ikegai Corp, cylinder temperature: 220° C., die temperature: 220° C.) and extruded to form a dispersion.

The obtained dispersion was combined with pure water (solvent) so that the dispersion content was 5% by weight (weight of dispersion/(weight of dispersion+weight of pure water)×100) or less, and the mixture was stirred at a temperature of 80° C. and a rotational speed of 100 rpm for 3 hours using a three-one motor (BL-3000 from Shinto Scientific Co., Ltd.). The solution obtained after stirring was filtered off with filter paper (No. 5A from Toyo Roshi Kaisha, Ltd.), and a filtered product was taken out. The taken-out filter product was again prepared using pure water so that the dispersion content was 5% by weight or less, and the operation in which the mixture was stirred at a temperature of 80° C. and a rotational speed of 100 rpm for 3 hours and filtered to take out a filter product was repeated three times or more, thus obtaining cellulose acetate particles.

The average particle size, particle size variation coefficient, sphericity, surface smoothness, bulk density, and plasticizer content of the obtained cellulose acetate particles were determined, and the biodegradability and the touch feeling of the obtained cellulose acetate particles were evaluated. The results are shown in Table 1. The average particle size, particle size variation coefficient, sphericity, surface smoothness, bulk density, plasticizer content, biodegradability and touch feeling were measured or evaluated by the following method.

Average Particle Size and Particle Size Variation Coefficient

The average particle size was measured using dynamic light scattering. First, the concentration of a sample was adjusted to about 100 ppm using pure water, and the sample was made into a pure water suspension using an ultrasonic vibration device. After that, the average particle size was measured by determining the volume frequency particle size distribution using a laser diffraction method (Horiba, Ltd. "Laser Diffraction/Scattering Particle Size Distribution Measurement Device LA-960", ultrasonication for 15 minutes, refractive index (1.500, medium (water; 1.333)). The average particle size (nm, etc.) herein was regarded as a value of the particle size corresponding to a cumulative 50% scattering intensity in the volume frequency particle size distribution. The particle size variation coefficient (%) was calculated by standard deviation of particle size/average particle size×100.

Sphericity

Major axis and minor axis of 30 randomly selected particles were measured using an image of particles observed with a scanning electron microscope (SEM), a minor axis/major axis ratio of each particle was determined, and an average value of the minor axis/major axis ratios was taken as the sphericity.

Surface Smoothness

Figure 1:
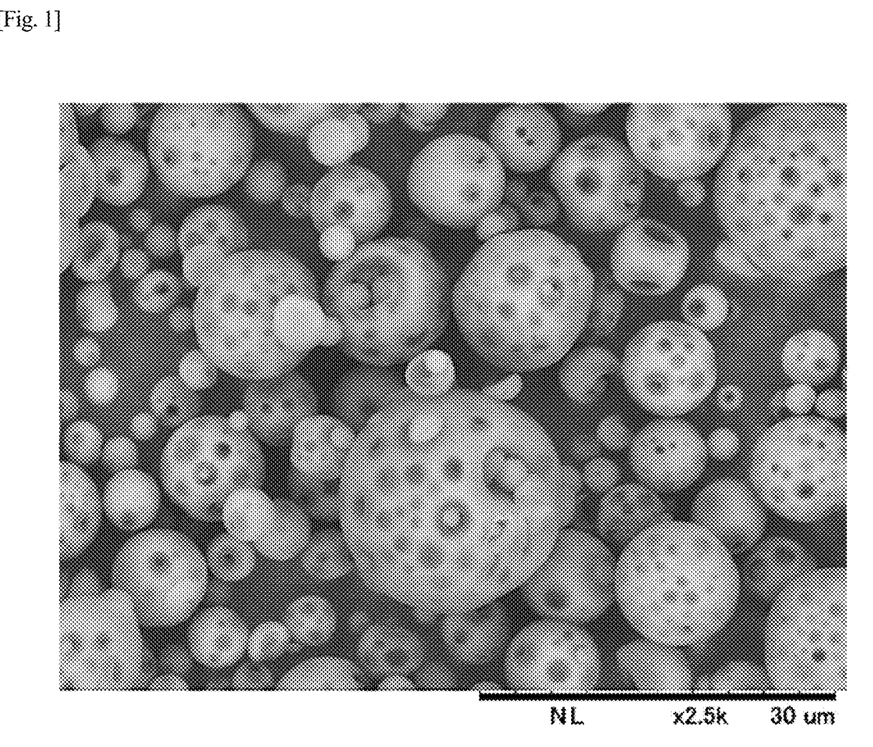
FIG. 1 is a view for explaining a method of evaluating surface smoothness (%).
Figure 2:
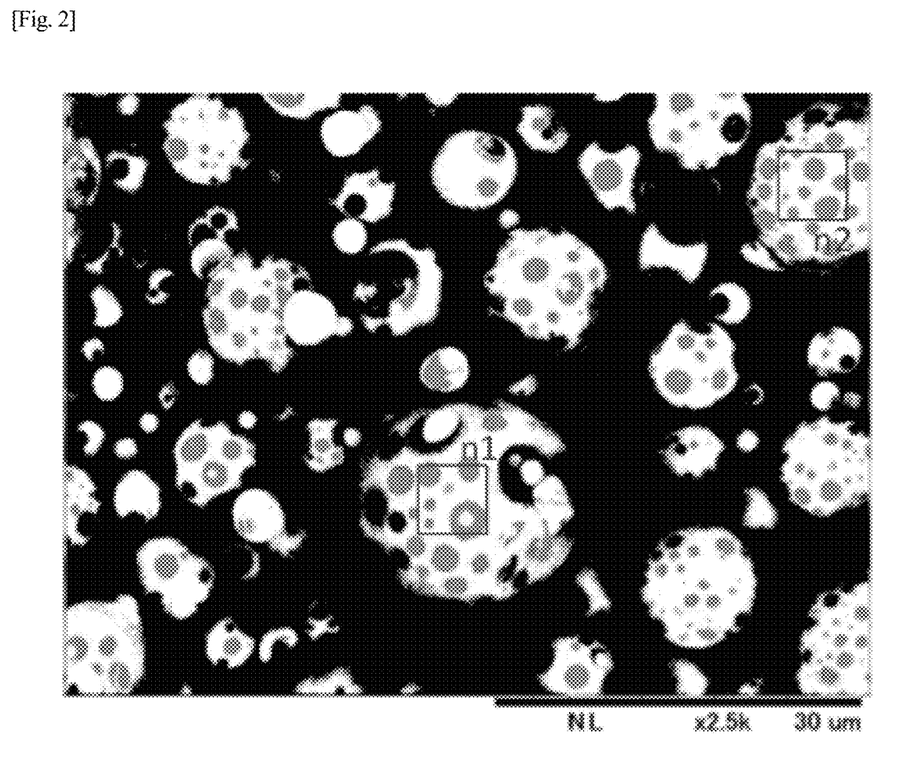
FIG. 2 is a view for explaining the method of evaluating the surface smoothness (%).

A scanning electron micrograph of 2500 to 5000 times of particles was taken (see FIG. 1 for an example of a photomicrograph of cellulose acetate particles), and an image was binarized using an image processor Winroof (from Mitani Corporation) (see FIG. 2 for an image obtained by binarizing the photomicrograph of FIG. 1). An arbitrary region smaller than the particle, including the center and/or near the center of one particle (e.g. regions designated n1 and n2 with reference to FIG. 2) may be used. The region may have a size of 5 μm square when the particle size is 15 μm. The area ratio of a portion (shade portion) corresponding to a recess of unevenness in the region was calculated, and the surface smoothness (%) of one of the particles was calculated by the following formula:

surface smoothness (%) of one particle=(1−concave area ratio)×100

Area ratio of recess=area of recess in the arbitrary region/the arbitrary area

The surface smoothness (%) was an average value of the surface smoothness of ten randomly selected particle samples, that is, n1 to 10. The higher the value, the higher the surface smoothness.

Bulk Density

The bulk density was measured according to "JIS K 1201-1."

Plasticizer Content

The plasticizer content (% by weight) was determined by $^1$H-NMR measurement.

Biodegradability

The biodegradability was assessed by the biodegradation rate. The biodegradation rate was measured by a method using activated sludge according to JIS K6950. The activated sludge was obtained from a municipal wastewater treatment plant. A supernatant (activated sludge concentration: about 360 ppm) obtained by leaving the activated sludge to stand for about 1 hour was used in an amount of about 300 ml per culture bottle. The measurement was started when 30 mg of the sample was stirred in the supernatant, and every 24 hours thereafter, the measurements were made a total of 31 times until after 720 hours, that is, after 30 days. The details of the measurement are as follows. Biochemical oxygen demand (BOD) in each culture bottle was measured using Coulometer OM3001 (from Okura Electric Co., Ltd.). A percentage of the biochemical oxygen demand (BOD) relative to theoretical biochemical oxygen demand (BOD) in complete decomposition based on the chemical composition of each sample was taken as the biodegradation rate (% by weight), and the biodegradability was evaluated as follows:

very good: more than 60% by weight, good: 40% by weight or more and 60% by weight or less, badish: 10% by weight or more and less than 40% by weight, bad: less than 10% by weight.

Touch Feeling

In terms of the touch feeling of particles, a sensory evaluation was made by a panel test conducted by 20 persons. When the persons touched the particles, they comprehensively evaluated both smoothness and a moist sensation based on the following criteria on a scale of 1 to 5. The average score of 20 persons was calculated.

Good: 5, goodish: 4, moderate: 3, badish: 2, bad: 1

Example A-2

Cellulose acetate particles were obtained in the same manner as in Example A-1 except that triacetin as a plasticizer was changed to acetyl triethyl citrate, the usage of a pellet of an obtained kneaded product was changed to 10 parts by weight, and the usage of polyvinyl alcohol was changed to 90 parts by weight.

Each physical property of the obtained cellulose acetate particles was evaluated by the above-mentioned measuring method. The results are shown in Table 1.

Example A-3

Cellulose acetate particles were obtained in the same manner as in Example A-1 except that the usage of a pellet of an obtained kneaded product was changed to 40 parts by weight and the usage of polyvinyl alcohol was changed to 60 parts by weight.

Each physical property of the obtained cellulose acetate particles was evaluated by the above-mentioned measuring method. The results are shown in Table 1.

Example A-4

Cellulose acetate particles were obtained in the same manner as in Example A-1 except that cellulose diacetate was changed to cellulose triacetate (from Daicel Corporation: total degree of acetyl substitution DS=2.8), triacetin was changed to diethyl phthalate, the usage of a pellet of an obtained kneaded product was changed to 40 parts by weight, the usage of polyvinyl alcohol was changed to 60 parts by weight, the cylinder temperature of a twin-screw extruder was changed to 240° C., and the die temperature was changed to 240° C.

Each physical property of the obtained cellulose acetate particles was evaluated by the above-mentioned measuring method. The results are shown in Table 1.

Example A-5

Cellulose acetate particles were obtained in the same manner as in Example A-1 except that triacetin as a plasticizer was changed to acetyl triethyl citrate.

Each physical property of the obtained cellulose acetate particles was evaluated by the above-mentioned measuring method. The results are shown in Table 1.

Example A-6

Cellulose acetate particles were obtained in the same manner as in Example A-1 except that cellulose diacetate (from Daicel Corporation: total degree of acetyl substitution DS=1.8) was used and triacetin as a plasticizer was changed to diacetin.

Each physical property of the obtained cellulose acetate particles was evaluated by the above-mentioned measuring method. The results are shown in Table 1.

Example A-7

Cellulose acetate particles were obtained in the same manner as in Example A-1 except that the usage of triacetin as a plasticizer was changed from 25 parts by weight to 20 parts by weight.

Each physical property of the obtained cellulose acetate particles was evaluated by the above-mentioned measuring method. The results are shown in Table 1.

Example A-8

100 parts by weight of cellulose diacetate (from Daicel Corporation: total degree of acetyl substitution DS=2.4) and 25 parts by weight of triacetin as a plasticizer were stirred and mixed using a Henschel mixer to obtain cellulose acetate impregnated with the plasticizer. Melt-kneading was not performed.

30 parts by weight of the obtained cellulose acetate impregnated with the plasticizer and 70 parts by weight of polyvinyl alcohol (from The Nippon Synthetic Chemical Industry Co., Ltd.: melting point 190° C., degree of saponification 99.1%) as a water-soluble polymer were dry blended and then supplied to a twin-screw extruder (PCM 30 from Ikegai Corp, cylinder temperature: 220° C., die temperature: 220° C.) and extruded to form a dispersion.

The obtained dispersion was combined with pure water (solvent) so that the dispersion content was 5% by weight (weight of dispersion/(weight of dispersion+weight of pure water)×100) or less, and the mixture was stirred at a temperature of 80° C. and a rotational speed of 100 rpm for 3 hours using a three-one motor (BL-3000 from Shinto Scientific Co., Ltd.). The solution obtained after stirring was filtered off with filter paper (No. 5A from Toyo Roshi Kaisha, Ltd.), and a filter product was taken out. The taken-out filter product was again prepared using pure water so that the dispersion content was 5% by weight or less, and the operation in which the mixture was stirred at a temperature of 80° C. and a rotational speed of 100 rpm for 3 hours and filtered to take out a filter product was repeated three times or more, thus obtaining cellulose acetate particles.

Each physical property of the obtained cellulose acetate particles was evaluated by the above-mentioned measuring method. The results are shown in Table 1.

Example A-9

A dispersion was formed in the same manner as in Example A-1 except that a kneaded product was obtained in the same manner as in Example A-1, the usage of a pellet of the obtained kneaded product was changed to 32 parts by weight, and the usage of polyvinyl alcohol was changed to 68 parts by weight, and cellulose acetate particles were obtained in the same manner as in Example A-1 except that the obtained dispersion was combined with pure water so that the dispersion content was 5% by weight or less, and the mixture was vigorously stirred at a temperature of 80° C. for 5 hours at a rotational speed (500 rpm) five times that of Example A-1.

Each physical property of the obtained cellulose acetate particles was evaluated by the above-mentioned measuring method. The results are shown in Table 1.

Example A-10

A dispersion was formed in the same manner as in Example A-1 except that a kneaded product was obtained in the same manner as in Example A-1 except that the usage of triacetin was changed to 22 parts by weight, the usage of a pellet of the obtained kneaded product was changed to 34 parts by weight, and the usage of polyvinyl alcohol was changed to 66 parts by weight, and cellulose acetate particles were obtained in the same manner as in Example A-1 except that the obtained dispersion was combined with pure water so that the dispersion content was 5% by weight or less, and the mixture was vigorously stirred at a temperature of 80° C. for 5 hours at a rotational speed (200 rpm) twice that of Example A-1.

Each physical property of the obtained cellulose acetate particles was evaluated by the above-mentioned measuring method. The results are shown in Table 1.

Example A-11

A dispersion was formed in the same manner as in Example A-1 except that a kneaded product was obtained in the same manner as in Example A-1, the usage of a pellet of the obtained kneaded product was changed to 32 parts by weight, 20 parts of glycerin was mixed with 80 parts of thermoplastic starch (from Sanwa Starch Co., Ltd.; pregelatinized tapioca starch) as a water-soluble polymer to make the amount 100 parts, and the usage of the water-soluble polymer was changed to 68 parts by weight, and cellulose acetate particles were obtained in the same manner as in Example A-1 except that the obtained dispersion was combined with pure water so that the dispersion content was 5% by weight (weight of dispersion/(weight of dispersion+ weight of pure water)×100) or less, and the mixture was vigorously stirred at a temperature of 80° C. for 5 hours at a rotational speed (500 rpm) five times that of Example A-1.

Each physical property of the obtained cellulose acetate particles was evaluated by the above-mentioned measuring method. The results are shown in Table 1.

Comparative Example A-1

Acrylic particles sold under the trademark MATSUMOTO MICROSPHERE® M-100 (from Matsumoto Yushi-Seiyaku Co., Ltd.) were used. Each physical property of the particles was evaluated by the above-mentioned measuring method. The results are shown in Table 1.

Comparative Example A-2

Nylon particles sold under the trademark TORAY NYLON® nylon 12 SP-500 (from Toray Industries, Inc.) were used. Each physical property of the particles was evaluated by the above-mentioned measuring method. The results are shown in Table 1.

Comparative Example A-3

As silicone particles, polymethylsilsesquioxane sold under KMP-591 (from Shin-Etsu Chemical Co., Ltd.) was used. Each physical property of the particles was evaluated by the above-mentioned measuring method. The results are shown in Table 1.

Comparative Example A-4

Cellulose particles sold under the trademark CELLULOSCRUB™ (from LESSONIA) were used. Each physical property of the particles was evaluated by the above-mentioned measuring method. The results are shown in Table 1.

Comparative Example A-5

Cellulose acetate particles sold under CELLUFLOW TA-25 (from JNC Corporation) were used. Each physical property of the particles was evaluated by the above-mentioned measuring method. The results are shown in Table 1.

TABLE 1

| | Example A-1 Cellulose acetate particles | Example A-2 Cellulose acetate particles | Example A-3 Cellulose acetate particles | Example A-4 Cellulose acetate particles | Example A-5 Cellulose acetate particles | Example A-6 Cellulose acetate particles | Example A-7 Cellulose acetate particles | Example A-8 Cellulose acetate particles |
|---|---|---|---|---|---|---|---|---|
| Total degree of acetyl substitution (DS) | 2.4 | 2.4 | 2.4 | 2.8 | 2.4 | 1.8 | 2.4 | 2.4 |
| Plasticizer | Triacetin | Acetyl triethyl citrate | Triacetin | Diethyl phthalate | Acetyl triethyl citrate | Diacetin | Triacetin | Triacetin |
| Average particle size | 4.2 μm | 100 nm | 14 μm | 20 μm | 1.1 μm | 2.6 μm | 32 μm | 4.8 μm |
| Particle size variation coefficient [%] | 38 | 42 | 41 | 40 | 37 | 39 | 38 | 44 |
| Sphericity | 0.98 | 0.94 | 0.97 | 0.95 | 0.97 | 0.97 | 0.96 | 0.83 |
| Surface smoothness [%] | 100 | 99 | 100 | 100 | 99 | 99 | 100 | 100 |
| Bulk density | 0.63 | 0.62 | 0.61 | 0.62 | 0.62 | 0.61 | 0.63 | 0.60 |
| Plasticizer content [wt %] | 16.0 | 13.2 | 16.7 | 16.0 | 18.0 | 15.5 | 13.2 | 15.7 |
| Biodegradability | Very good | Very good | Very good | Badish | Very good | Very good | Very good | Very good |
| Touch feeling | 4.8 | 4.2 | 4.5 | 4.6 | 4.5 | 4.7 | 4.4 | 4.2 |

| | Example A-9 Cellulose acetate particles | Example A-10 Cellulose acetate particles | Example A-11 Cellulose acetate particles | Comparative Example A-1 Acrylic particles | Comparative Example A-2 Nylon particles | Comparative Example A-3 Silicone particles | Comparative Example A-4 Cellulose particles | Comparative Example A-5 Cellulose acetate particles |
|---|---|---|---|---|---|---|---|---|
| Total degree of acetyl substitution (DS) | 2.4 | 2.4 | 2.4 | — | — | — | — | — |
| Plasticizer | Triacetin | Triacetin | Triacetin | — | — | — | — | — |
| Average particle size | 5.2 μm | 7.1 μm | 6.8 μm | 8.1 μm | 5.0 μm | 6.4 μm | 330 μm | 7.3 μm |
| Particle size variation coefficient [%] | 36 | 37 | 39 | 35 | 32 | 30 | 63 | 38 |
| Sphericity | 0.98 | 0.97 | 0.95 | 0.95 | 0.67 | 0.96 | 0.77 | 0.91 |
| Surface smoothness [%] | 100 | 100 | 100 | 100 | 100 | 100 | 63 | 72 |

TABLE 1-continued

| | | | | | | | | |
|---|---|---|---|---|---|---|---|---|
| Bulk density | 0.60 | 0.58 | 0.58 | 0.61 | 0.23 | 0.65 | 0.58 | 0.33 |
| Plasticizer content [wt %] | <0.01 | <0.02 | <0.01 | — | — | — | — | No data |
| Biodegradability | Very good | Very good | Very good | Bad | Bad | Bad | Very good | Very good |
| Touch feeling | 4.6 | 4.8 | 4.4 | 3.5 | 4.5 | 4.1 | 1.6 | 2.7 |

As shown in Table 1, the cellulose acetate particles of Examples all have excellent biodegradability and excellent touch feeling.

Example B-1

Preparation of Liquid Foundation

Each component shown in Table 2 was mixed, then stirred well, and filled in a container to prepare liquid foundation. The touch feeling of the obtained liquid foundation was evaluated by the following method. The results are shown in Table 10.

TABLE 2

| Component | Product name, etc. | wt % |
|---|---|---|
| Cyclopentasiloxane | KF-995 (Shin-Etsu Chemical Co., Ltd.) | 15.2 |
| Mineral oil | HICALL K-230 (Kaneda Co., Ltd.) | 5.0 |
| Ethylhexyl methoxycinnamate | Uvinul MC80 (BASF) | 4.0 |
| Isononyl isononanoate | KAK-99 (Kokyu Alcohol Kogyo Co., Ltd.) | 3.0 |
| Disteardimonium hectorite, cyclopentasiloxane, etc. | Bentone Gel VS-5 PC V HV (Elementis) | 3.0 |
| Macadamia nut fatty acid phytostelyl | Plandool-MAS (Nippon Fine Chemical) | 0.3 |
| Trimethylsiloxy silicic acid, polypropylsilsesquioxane | MQ-1640 Flake Resin (Dow Corning Toray Co., Ltd.) | 0.3 |
| PEG-10 dimethicone | KF-6017P (Shin-Etsu Chemical Co., Ltd.) | 1.5 |
| Polyglyceryl-2 oleate, polyhydroxystearic acid, polyglyceryl-2 stearate | PolyAquol OS2 (innovacos) | 1.0 |
| Titanium oxide, cyclopentasiloxane, etc. | SDL-Ti70 (Daito Kasei Kogyo Co., Ltd.) | 12.3 |
| Iron oxide, cyclopentasiloxane, etc. | SDL-IOY50 (Daito Kasei Kogyo Co., Ltd.) SDL-IOR50 (Daito Kasei Kogyo Co., Ltd.) SDL-IOB50 (Daito Kasei Kogyo Co., Ltd.) | 3.0 |
| Example A-1: Cellulose acetate particles | | 3.0 |
| BG | 1,3-BG (UK) (Daicel Corporation) | 6.0 |
| Phenoxyethanol | Phenoxyethanol-SP (Yokkaichi Chemical Company, Limited.) | 0.3 |
| Sodium chloride | | 1.0 |
| EDTA-2Na | | 0.03 |
| Purified water | | Remaining amount |
| Total | | 100.0 |

Touch Feeling

In terms of a composition prepared by adding particles, a sensory evaluation was made by a panel test conducted by 20 persons. When the persons used each composition, they comprehensively evaluated both smoothness and a moist sensation based on the following criteria on a scale of 1 to 5. The average score of 20 persons was calculated.

Good: 5, goodish: 4, moderate: 3, badish: 2, bad: 1

Example B-2

Preparation of Sunscreen

Each component shown in Table 3 was mixed, then stirred well, and filled in a container to prepare a sunscreen. The touch feeling of the obtained sunscreen was evaluated by the above-mentioned method. The results are shown in Table 10.

TABLE 3

| Component | Product name, etc. | wt % |
|---|---|---|
| Diethylamino hydroxybenzoyl hexyl benzoate | Uvinul A Plus Glanular (BASF) | 2.00 |
| Bis-ethylhexyloxyphenol methoxyphenyl triazine | Tnosorb S (BASF) | 0.50 |
| Ethylhexyl methoxycinnamate, BHT | Uvinul MC80 (BASF) | 7.00 |
| Sebacate diisopropyl | IPSE (Nippon Fine Chemical) | 10.00 |
| Dimethicone | KF-96A-10CS (Shin-Etsu Chemical Co., Ltd.) | 2.00 |
| Isododecane | Marukasol R (Maruzen Petrochemical Co., Ltd.) | 26.47 |
| Trimethylsiloxy silicic acid | MQ-1640 Flake Resin (Dow Corning Toray Co., Ltd.) | 1.00 |
| PEG-9 polydimethylsiloxyethyl dimethicone | KF-6028 (Shin-Etsu Chemical Co., Ltd.) | 2.00 |
| Titanium oxide, etc. | DIS-OP-10A (Sakai Chemical Industry Co., Ltd.) | 4.00 |
| Zinc oxide, etc. | DIF-OP-3W (Sakai Chemical Industry Co., Ltd.) | 10.00 |
| Example A-1: Cellulose acetate particles | | 5.00 |
| Purified water | | 19.30 |
| BG | 1,3-BG (UK) (Daicel Corporation) | 3.00 |
| Phenoxyethanol | Phenoxyethanol-SP (Yokkaichi Chemical Company, Limited.) | 0.20 |
| Ethanol | | 7.00 |
| Sodium chloride | | 0.50 |
| EDTA-2Na | | 0.03 |
| Total | | 100.0 |

Example B-3

Preparation of Powder Foundation

After a component A shown in Table 4 was roughly mixed, a uniformly dissolved component B was added and well stirred, and then the mixture was filled in a container to prepare powder foundation. The touch feeling of the obtained powder foundation was evaluated by the above-mentioned method. The results are shown in Table 10.

TABLE 4

| Component | wt % |
|---|---|
| (Component A) | |
| Example A-1: Cellulose acetate particles | 7.50 |
| SI01-2 talc JA-46R | 29.67 |
| Mica Y-2300 | 20.00 |
| SI01-2 sericite FSE | 33.00 |
| SI01-2 titanium oxide CR-50 | 6.50 |
| SI-2 yellow iron oxide LLXLO | 2.30 |

TABLE 4-continued

| Component | wt % |
|---|---|
| SI-2 red iron oxide RED R-516L | 0.59 |
| SI-2 black iron oxide BL-100 | 0.44 |
| Component A total (Component B) | 100.00 |
| Dimethicone (20) | 20.00 |
| Dimethicone (350) | 20.00 |
| Glyceryl isostearate | 7.20 |
| Triethylhexanoin | 17.00 |
| Octyldodecyl oleate | 31.55 |
| Sorbitan stearate | 1.00 |
| Polyglyceryl-2 oleate | 3.10 |
| Propylparaben | 0.10 |
| Tocopherol | 0.05 |
| Component B total (Final blending) | 100.0 |
| Component A | 90.00 |
| Component B | 100.00 |

Example B-4

Preparation of Makeup Base

A component C shown in Table 5 was dispersed in the component A and stirred well. The component B was added, stirred and filled in a container to prepare a makeup base. The touch feeling of the obtained makeup base was evaluated by the above-mentioned method. The results are shown in Table 10.

TABLE 5

| Component | wt % |
|---|---|
| (Component A) | |
| (Dimethicone/(PEG-10/15)) cross polymer, dimethicone | 3.50 |
| PEG-9 polydimethylsiloxyethyl dimethicone | 2.00 |
| Dimethicone | 5.00 |
| Isononyl isononanoate | 4.50 |
| Octyl methoxycinnamate | 10.00 |
| Quaternium-18 hectorite | 1.20 |
| (Dimethicone/vinyl dimethicone) cross polymer, dimethicone | 5.00 |
| Cyclomethicone | 25.00 |
| (Component B) | |
| Purified water | Remaining amount |
| 1,3-butylene glycol | 5.00 |
| Sodium citrate | 0.20 |
| Antiseptic | 0.30 |
| (Component C) | |
| Example A-1: Cellulose acetate particles | 10.00 |
| Total | 100.0 |

Example B-5

Preparation of Lip Primer

The component B shown in Table 6 was heated to 60° C. and mixed well. The component C was added thereto and dispersed well. In addition, the component A was added, dissolved using a microwave, and then mixed well. Then, the mixture was heated and dissolved using a microwave again, poured into a mold, and solidified by cooling. The resultant product was set in a lipstick container to prepare a lip primer. The touch feeling of the obtained lip primer was evaluated by the above-mentioned method. The results are shown in Table 10.

TABLE 6

| Component | wt % |
|---|---|
| (Component A) | |
| Ceresin | 4.27 |
| Microcrystalline wax | 1.55 |
| Deresin candelilla wax | 5.03 |
| High boiling point paraffin | 3.07 |
| (Component B) | |
| Diisostealyl malate | 1.95 |
| Dipentaelythritol fatty acid ester | 6.22 |
| Adsorption purified lanolin | 2.52 |
| Acetylated liquid lanolin | 13.34 |
| Glyceryl tri-2-ethylhexanoate | 19.02 |
| Liquid paraffin | 7.28 |
| Isotridecyl isononanoate | 3.21 |
| Diglycelyl triisostearate | 4.01 |
| Methylphenyl polysiloxane | 2.41 |
| Para-hydroxybenzoate | 0.07 |
| Diisostealyl malate | Remaining amount |
| Natural type vitamine E | 0.05 |
| (Component C) | |
| Example A-1: Cellulose acetate particles | 10.00 |
| Total | 100.00 |

Example B-6

Preparation of Body Powder

The component A shown in Table 7 was mixed well using a mixer. The obtained powder was filled in a container to prepare a body powder. The touch feeling of the obtained body powder was evaluated by the above-mentioned method. The results are shown in Table 10.

TABLE 7

| Component | wt % |
|---|---|
| (ComponentA) | |
| Talc | Remaining amount |
| Example A-1: Cellulose acetate particles | 10.00 |
| Aromatic | Suitable amount |
| Total | 100.00 |

Example B-7

Preparation of Solid Face Powder

The solid face powder of the present invention conforms to a conventional cosmetic production method. That is, talc and a color pigment shown in Table 8 were mixed in a blender. In addition, all powder portions including cellulose acetate particles and the color pigment and talc mixed previously in a blender were stirred using a Henschel mixer. Thereafter, an oil component (binder) was added, the mixture was heated to 70° C. and further stirred, and then a grinding step was performed as necessary. The resultant product was compression-molded into a container of a gold dish to prepare a solid face powder. The touch feeling of the obtained solid face powder was evaluated by the above-mentioned method. The results are shown in Table 10.

TABLE 8

| Component | wt % |
|---|---|
| (Powder) | |
| Talc | 30.00 |
| Sericite | 20.00 |
| Kaolin | 15.00 |
| Titanium dioxide | 5.00 |
| Zinc myristate | 5.00 |
| Magnesium carbonate | 5.00 |
| Color pigment | Suitable amount |
| Example A-1: Cellulose acetate particles | 15.00 |
| (Binder) | |
| Tragacanth gum | 3.00 |
| Liquid paraffin | 2.00 |
| Others: antiseptic, antioxidant, and aromatic are added in a suitable amount as necessary. | |
| Total | 100.00 |

Example B-8

Preparation of Solid Powder Eye Shadow

After a powder shown in Table 9 was thoroughly mixed, a binder was uniformly dissolved, added to a powder portion, further mixed, and then compression-molded to prepare a solid powder eye shadow. The touch feeling of the obtained solid powder eye shadow was evaluated by the above-mentioned method. The results are shown in Table 10.

TABLE 9

| Component | wt % |
|---|---|
| (Powder) | |
| Mica | 15.00 |
| Sericite | 5.00 |
| Pigment | 15.00 |
| Pearl pigment | 10.00 |
| Example A-1: Cellulose acetate particles | 51.00 |
| (Binder) | |
| Methylpolysiloxane | 2.00 |
| (Other) | |
| Sorbitan sesquioleate | 2.00 |
| Others: antioxidant, aromatic, and antiseptic are added in a suitable amount as necessary. | |
| Total | 100.00 |

Example B-9

Liquid foundation was prepared in the same manner as in Example B-1 except that the cellulose acetate particles in Example A-1 in Table 2 were changed to the cellulose acetate particles in Example A-5. The touch feeling of the obtained liquid foundation was evaluated by the above-mentioned method. The results are shown in Table 10.

Example B-10

A sunscreen was prepared in the same manner as in Example B-2 except that the cellulose acetate particles in Example A-1 in Table 3 were changed to the cellulose acetate particles in Example A-5. The touch feeling of the obtained sunscreen was evaluated by the above-mentioned method. The results are shown in Table 10.

Example B-11

Powder foundation was prepared in the same manner as in Example B-3 except that the cellulose acetate particles in Example A-1 in Table 4 were changed to the cellulose acetate particles in Example A-5. The touch feeling of the obtained powder foundation was evaluated by the above-mentioned method. The results are shown in Table 10.

Example B-12

A makeup base was prepared in the same manner as in Example B-4 except that the cellulose acetate particles in Example A-1 in Table 5 were changed to the cellulose acetate particles in Example A-5. The touch feeling of the obtained makeup base was evaluated by the above-mentioned method. The results are shown in Table 10.

Example B-13

Liquid foundation was prepared in the same manner as in Example B-1 except that the cellulose acetate particles in Example A-1 in Table 2 were changed to the cellulose acetate particles in Example A-6. The touch feeling of the obtained liquid foundation was evaluated by the above-mentioned method. The results are shown in Table 10.

Example B-14

A sunscreen was prepared in the same manner as in Example B-2 except that the cellulose acetate particles in Example A-1 in Table 3 were changed to the cellulose acetate particles in Example A-6. The touch feeling of the obtained sunscreen was evaluated by the above-mentioned method. The results are shown in Table 10.

Example B-15

Liquid foundation was prepared in the same manner as in Example B-1 except that the cellulose acetate particles in Example A-1 in Table 2 were changed to the cellulose acetate particles in Example A-7. The touch feeling of the obtained liquid foundation was evaluated by the above-mentioned method. The results are shown in Table 10.

Example B-16

A sunscreen was prepared in the same manner as in Example B-2 except that the cellulose acetate particles in Example A-1 in Table 3 were changed to the cellulose acetate particles in Example A-7. The touch feeling of the obtained sunscreen was evaluated by the above-mentioned method. The results are shown in Table 10.

Example B-17

Liquid foundation was prepared in the same manner as in Example B-1 except that cyclopentasiloxane in Table 2 was changed to a mixture obtained by mixing dodecane (PARAFOL 12-97 (Sasol)) and Cetiol Ultimate (undecane:tridecane=65% by weight: 35% by weight, from BASF SE) of the same weight, isononyl isononanoate was changed to a mixture obtained by mixing coco-caprylate (Cetiol C5 (BASF)), coco-caprylate/caprate (Cetiol C5C (BASF)), and dicaprylyl carbonate (Cethiol CC (BASF)) of the same weight, and macadamia nut fatty acid phytosteryl was changed to camellia oil (pure camellia oil (Nikko Rica Corporation)). The touch feeling of the obtained liquid foundation was evaluated by the above-mentioned method. The results are shown in Table 10.

Example B-18

A sunscreen was prepared in the same manner as in Example B-2 except that isododecane in Table 3 was changed to a mixture obtained by mixing dodecane (PARAFOL 12-97 (Sasol)) and Cetiol Ultimate (undecane:tridecane=65% by weight: 35% by weight, from BASF SE) of the same weight, and sebacate diisopropyl was changed to a mixture obtained by mixing coco-caprylate (Cetiol C5 (BASF)), coco-caprylate/caprate (Cetiol C5C (BASF)), and dicaprylyl carbonate (Cethiol CC (BASF)) of the same weight. The touch feeling of the obtained sunscreen was evaluated by the above-mentioned method. The results are shown in Table 10.

Example B-19

Powder foundation was prepared in the same manner as in Example B-3 except that dimethicone in Table 4 was changed to a mixture obtained by mixing dodecane (PARAFOL 12-97 (Sasol)) and Cetiol Ultimate (undecane:tridecane=65% by weight: 35% by weight, from BASF SE) of the same weight, and octyldodecyl oleate was changed to a mixture obtained by mixing coco-caprylate (Cetiol C5 (BASF)), coco-caprylate/caprate (Cetiol C5C (BASF)), and dicaprylyl carbonate (Cethiol CC (BASF)) of the same weight. The touch feeling of the obtained powder foundation was evaluated by the above-mentioned method. The results are shown in Table 10.

Example B-20

A makeup base was prepared in the same manner as in Example B-4 except that cyclomethicone in Table 5 was changed to a mixture obtained by mixing dodecane (PARAFOL 12-97 (Sasol)) and Cetiol Ultimate (undecane:tridecane=65% by weight: 35% by weight, from BASF SE) of the same weight, and isononyl isononanoate was changed to a mixture obtained by mixing coco-caprylate (Cetiol C5 (BASF)), coco-caprylate/caprate (Cetiol C5C (BASF)), and dicaprylyl carbonate (Cethiol CC (BASF)) of the same weight. The touch feeling of the obtained makeup base was evaluated by the above-mentioned method. The results are shown in Table 10.

Example B-21

Powder foundation was prepared in the same manner as in Example B-3 except that Mica Y-2300X in Table 4 was changed to a mixture obtained by mixing mica (Mica Y-2300X (Yamaguchi Mica Co., Ltd.)), synthetic mica (PDM-10L (Topy Industries Limited)), and (fluorinated/hydroxylated/oxidized)/(Mg/K/silicon) (Micro Mica MK-200K (Katakura & Co-op Agri Corporation) of the same weight, sericite was changed to a mixture obtained by mixing barium sulfate (plate-like barium sulfate H (from Sakai Chemical Industry Co., Ltd.)) and boron nitride (SHP-6 (Mizushima Ferroalloy Co., Ltd.)) of the same weight, and talc was changed to a mixture obtained by mixing cellulose (NP fiber W-06MG (Nippon Paper Industries Co., Ltd.)) and silica (Godball E-16C (Suzuki Yushi Kogyo)) of the same weight. The touch feeling of the obtained powder foundation was evaluated by the above-mentioned method. The results are shown in Table 10.

Example B-22

A body powder was prepared in the same manner as in Example B-6 except that talc in Table 7 was changed to a mixture obtained by mixing cellulose (NP fiber W-06MG (Nippon Paper Industries Co., Ltd.)) and silica (Godball E-16C (Suzuki Yushi Kogyo)) of the same weight. The touch feeling of the obtained body powder was evaluated by the above-mentioned method. The results are shown in Table 10.

Example B-23

A solid powder eye shadow was prepared in the same manner as in Example B-8 except that Mica Y-2300X in Table 9 was changed to a mixture obtained by mixing mica (Mica Y-2300X (Yamaguchi Mica Co., Ltd.)), synthetic mica (PDM-10L (Topy Industries Limited)), and (fluorinated/hydroxylated/oxidized)/(Mg/K/silicon) (Micro Mica MK-200K (Katakura & Co-op Agri Corporation) of the same weight, and sericite was changed to a mixture obtained by mixing barium sulfate (plate-like barium sulfate H (from Sakai Chemical Industry Co., Ltd.)) and boron nitride (SHP-6 (Mizushima Ferroalloy Co., Ltd.)) of the same weight. The touch feeling of the obtained solid powder eye shadow was evaluated by the above-mentioned method. The results are shown in Table 10.

Example B-24

Liquid foundation was prepared in the same manner as in Example B-1 except that BG in Table 2 was changed to a mixture obtained by mixing glycerin and pentylene glycol (Diol PD (Kokyu Alcohol Kogyo Co., Ltd.)) of the same weight. The touch feeling of the obtained liquid foundation was evaluated by the above-mentioned method. The results are shown in Table 10.

Example B-25

A sunscreen was prepared in the same manner as in Example B-2 except that BG in Table 3 was changed to a mixture obtained by mixing glycerin and pentylene glycol (Diol PD (Kokyu Alcohol Kogyo Co., Ltd.)) of the same weight. The touch feeling of the obtained sunscreen was evaluated by the above-mentioned method. The results are shown in Table 10.

Example B-26

A makeup base was prepared in the same manner as in Example B-4 except that 1.3-butylene glycol in Table 5 was changed to a mixture obtained by mixing glycerin and pentylene glycol (Diol PD (Kokyu Alcohol Kogyo Co., Ltd.)) of the same weight. The touch feeling of the obtained makeup base was evaluated by the above-mentioned method. The results are shown in Table 10.

Comparative Examples B-1 to 8

In Comparative Examples B-1 to 8, liquid foundation, a sunscreen, powder foundation, a makeup base, a lip primer, a body powder, a solid face powder, and a solid powder eye shadow were prepared in the same manner as in Examples B-1 to 8 except that the cellulose acetate particles in Example A-1 in Tables 2 to 9 were changed to the acrylic particles in Comparative Example A-1. Each touch feeling was evaluated by the above-mentioned method. The results are shown in Table 11.

TABLE 10

|  | Example B-1 | Example B-2 | Example B-3 | Example B-4 | Example B-5 | Example B-6 | Example B-7 | Example B-8 |
|---|---|---|---|---|---|---|---|---|
| Composition | Liquid foundation | Sunscreen | Powder foundation | Makeup base | Lip primer | Body powder | Solid face powder | Solid powder eye shadow |
| Particles | Example A-1 | Example A-1 | Example A-1 | Example A-1 | Example A-1 | Example A-1 | Example A-1 | Example A-1 |
| Touch feeling | 4.1 | 4.5 | 4.3 | 4.2 | 4.1 | 4.5 | 4.7 | 4.6 |
|  | Example B-9 | Example B-10 | Example B-11 | Example B-12 | Example B-13 | Example B-14 | Example B-15 | Example B-16 |
| Composition | Liquid foundation | Sunscreen | Powder foundation | Makeup base | Liquid foundation | Sunscreen | Liquid foundation | Sunscreen |
| Particles | Example A-5 | Example A-5 | Example A-5 | Example A-5 | Example A-6 | Example A-6 | Example A-7 | Example A-7 |
| Touch feeling | 4.5 | 4.2 | 4.1 | 4.1 | 4.3 | 4.4 | 4.1 | 4.1 |
|  | Example B-17 | Example B-18 | Example B-19 | Example B-20 | Example B-21 | Example B-22 | Example B-23 | Example B-24 |
| Composition | Liquid foundation | Sunscreen | Powder foundation | Makeup base | Powder foundation | Body powder | Solid powder eye shadow | Liquid foundation |
| Particles | Example A-1 | Example A-1 | Example A-1 | Example A-1 | Example A-1 | Example A-1 | Example A-1 | Example A-1 |
| Touch feeling | 4.2 | 4.3 | 4.2 | 4.1 | 4.2 | 4.4 | 4.2 | 4.3 |
|  | Example B-25 | Example B-26 |  |  |  |  |  |  |
| Composition | Sunscreen | Makeup base |  |  |  |  |  |  |
| Particles | Example A-1 | Example A-1 |  |  |  |  |  |  |
| Touch feeling | 4.3 | 4.3 |  |  |  |  |  |  |

TABLE 11

|  | Comparative Example B-1 | Comparative Example B-2 | Comparative Example B-3 | Comparative Example B-4 | Comparative Example B-5 | Comparative Example B-6 | Comparative Example B-7 | Comparative Example B-8 |
|---|---|---|---|---|---|---|---|---|
| Composition | Liquid foundation | Sunscreen | Powder foundation | Makeup base | Lip primer | Body powder | Solid face powder | Solid powder eye shadow |
| Particles | Comparative Example A-1 | Comparative Example A-1 | Comparative Example A-1 | Comparative Example A-1 | Comparative Example A-1 | Comparative Example A-1 | Comparative Example A-1 | Comparative Example A-1 |
| Touch feeling | 3.5 | 3.4 | 3.5 | 3.4 | 3.3 | 3.2 | 3.7 | 3.6 |

As shown in Tables 10 and 11, the touch feeling of the cosmetic compositions containing the cellulose acetate particles of Examples B-1 to 26 is all 4.0 or more and is excellent. Since the cosmetic compositions all contain cellulose acetate particles, they have excellent biodegradability.

The invention claimed is:

1. Cellulose acetate particles having an average particle size of 80 nm to 80 μm, a sphericity of 0.7 to 1.0, a surface smoothness of 80% to 100%, and the cellulose acetate having a total degree of acetyl substitution of 0.7 to 2.9.

2. The cellulose acetate particles according to claim 1, wherein the total degree of acetyl substitution of the cellulose acetate is 2.0 to less than 2.6.

3. The cellulose acetate particles according to claim 1, wherein the cellulose acetate particles further comprise a plasticizer, and a content of the plasticizer is 2% by weight to 40% by weight based on a weight of the cellulose acetate particles.

4. The cellulose acetate particles according to claim 3, wherein the plasticizer is at least one selected from the group consisting of a citric acid-based plasticizer, a glycerin ester-based plasticizer, an adipic acid-based plasticizer, and a phthalic acid-based plasticizer.

5. The cellulose acetate particles according to claim 1, having a particle size variation coefficient of 0% to 60%.

6. The cellulose acetate particles according to claim 1, wherein the sphericity is 0.8 to 1.0.

7. The cellulose acetate particles according to claim 1, wherein the sphericity is 0.9 to 1.0.

8. The cellulose acetate particles according to claim 1, wherein the surface smoothness is 85% to 100%.

9. The cellulose acetate particles according to claim 1, wherein the surface smoothness is 90% to 100%.

10. The cellulose acetate particles according to claim 1, wherein the average particle size is 100 nm to 40 μm.

11. The cellulose acetate particles according to claim 1, having a bulk density of 0.1 to 0.9 g/cm$^3$.

12. The cellulose acetate particles according to claim 1, having a bulk density of 0.5 to 0.9 g/cm$^3$.

13. The cellulose acetate particles according to claim 1, wherein the average particle size is 1 μm to 80 μm.

14. A cosmetic composition containing the cellulose acetate particles according to claim 1.

15. The cellulose acetate particles according to claim 1, wherein the cellulose acetate particles are produced by a process comprising:
mixing cellulose acetate having a total degree of acetyl substitution of 0.7 to 2.9 with a plasticizer to obtain cellulose acetate impregnated with the plasticizer;
kneading the cellulose acetate impregnated with the plasticizer and a water-soluble polymer at 200° C. to 280° C. to obtain a dispersion having the cellulose acetate impregnated with the plasticizer as a dispersoid; and
removing the water-soluble polymer from the dispersion.

16. A method of producing cellulose acetate particles according to claim 1, the method comprising:
mixing cellulose acetate having a total degree of acetyl substitution of 0.7 to 2.9 with a plasticizer to obtain cellulose acetate impregnated with the plasticizer;
kneading the cellulose acetate impregnated with the plasticizer and a water-soluble polymer at 200° C. to 280° C. to obtain a dispersion having the cellulose acetate impregnated with the plasticizer as a dispersoid; and
removing the water-soluble polymer from the dispersion.

17. The method according to claim 16, wherein the mixing is performed by mixing the cellulose acetate and the plasticizer in a temperature range of 20° C. to less than 200° C. and then melt-kneading.

18. The method according to claim 16, wherein the plasticizer is at least one selected from the group consisting of a citric acid-based plasticizer, a glycerin ester-based plasticizer, an adipic acid-based plasticizer, and a phthalic acid-based plasticizer.

19. The method according to claim 16, wherein the plasticizer is at least one selected from the group consisting of triethyl citrate, acetyl triethyl citrate, acetyl tributyl citrate, triacetin, and diisononyl adipate.

20. The method according to claim 16, wherein the plasticizer is at least one selected from the group consisting of acetyl triethyl citrate, triacetin, diacetin, and diethyl phthalate.

21. The method according to claim 16, wherein the water-soluble polymer is polyvinyl alcohol or thermoplastic starch.

22. The method according to claim 16, wherein the amount of the plasticizer to be added to obtain the cellulose acetate impregnated with the plasticizer is more than 0 parts by weight to 40 parts by weight with respect to 100 parts by weight of the total of the cellulose acetate and the plasticizer.

23. The method according to claim 16, wherein the amount of the plasticizer to be added to obtain the cellulose acetate impregnated with the plasticizer is 10 parts by weight to 30 parts by weight with respect to 100 parts by weight of the total of the cellulose acetate and the plasticizer.

24. The method according to claim 16, wherein the amount of the water-soluble polymer to be added to obtain the dispersion having the cellulose acetate impregnated with the plasticizer as a dispersoid is 55 parts by weight to 99 parts by weight with respect to 100 parts by weight of the total of the cellulose acetate impregnated with the plasticizer and the water-soluble polymer.

25. The method according to claim 16, wherein the amount of the water-soluble polymer to be added to obtain the dispersion having the cellulose acetate impregnated with the plasticizer as a dispersoid is 60 parts by weight to 90 parts by weight with respect to 100 parts by weight of the total of the cellulose acetate impregnated with the plasticizer and the water-soluble polymer.

* * * * *